United States Patent [19]
Grieveson et al.

[11] Patent Number: 5,661,189
[45] Date of Patent: Aug. 26, 1997

[54] DETERGENT COMPOSITION

[75] Inventors: Ailsa Pauline Hilary Grieveson, Heswall; Margaret Jobling, Bebington, both of Great Britain; Shiji Shen; Liang Sheng Tsaur, both of Norwood, N.J.

[73] Assignee: Lever Brothers Company, Division of Conopco, Inc., New York, N.Y.

[21] Appl. No.: 469,326

[22] Filed: Jun. 6, 1995

[30] Foreign Application Priority Data

Jul. 19, 1994 [GB] United Kingdom ............... 9414574

[51] Int. Cl.$^6$ ................................... A61K 31/74
[52] U.S. Cl. ................ 514/784; 424/78.03; 512/1; 510/158; 514/846
[58] Field of Search ............... 252/89.1; 514/846; 424/78.03; 512/1

[56] References Cited

FOREIGN PATENT DOCUMENTS

| | | |
|---|---|---|
| 0268982 | 6/1988 | European Pat. Off. . |
| 0407042 | 1/1991 | European Pat. Off. . |
| 0413417 | 2/1991 | European Pat. Off. . |
| 0452202 | 10/1991 | European Pat. Off. . |
| 0485212 | 5/1992 | European Pat. Off. . |
| 0552024 | 7/1993 | European Pat. Off. . |
| 90/13283 | 11/1990 | WIPO . |
| 93/09761 | 5/1993 | WIPO . |
| 93/19149 | 9/1993 | WIPO . |
| 93/21293 | 10/1993 | WIPO . |
| 94/01084 | 1/1994 | WIPO . |
| 94/01085 | 1/1994 | WIPO . |
| 94/03152 | 2/1994 | WIPO . |
| 94/17166 | 8/1994 | WIPO . |
| 96/17592 | 3/1996 | WIPO . |
| 96/17591 | 6/1996 | WIPO . |

Primary Examiner—Terressa Mosley
Attorney, Agent, or Firm—Ronald A. Koatz

[57] ABSTRACT

An aqueous liquid cleansing and moisturising composition comprising a surface active agent selected from anionic, nonionic, zwitterionic and cationic surface active agents and mixtures thereof; an benefit agent having a weight average particle size in the range 50 to 500 microns; and a thickening agent. The thickening agent is added to the benefit agent in amount from 1 to 50% wt, based on the benefit agent.

10 Claims, No Drawings

DETERGENT COMPOSITION

The present invention relates to detergent compositions suitable for care and personal washing of the skin. In particular, it relates to compositions which are formulated to give mild cleansing and conditioning of the skin.

Compositions formulated to cleanse the skin are well known. It is also known to formulate products which provide both a cleansing and a moisturising benefit.

For example WO 90/13283 discloses a composition comprising an acyl ester of an isethionic acid salt, a long chain fatty acid, a moisturiser component and, optionally, soap.

One of the problems which may be encountered with such dual purpose compositions is that, whilst cleansing may be effective, there is an insufficient level of moisturising.

We have found a way of formulating such compositions such that they can deliver effective moisturising, conditioning or protection of the skin.

In WO 94/01085 and 94/01084 the advantage of depositing large particles of petrolatum from soap based compositions is recognised.

However, according to WO 94/03152, concerned with shower gels comprising, a non-soap detergent, silicone oil added to condition the skin and cationic polymers, the maximum average droplet size of the silicone oil that can be used is 2 microns, if product stability is to be maintained.

We have now found that larger particles, by particle is meant a solid particle or liquid droplet, of benefit agent can be incorporated into non-soap based compositions and effective delivery of the benefit agent can be achieved if the benefit agent is thickened.

Thus, according to the invention there is provided an aqueous liquid cleansing and moisturising composition comprising:
  a) a surface active agent selected from anionic, nonionic, zwitterionic and cationic surface active agents, and mixtures thereof;
  b) an benefit agent having a weight average particle size in the range 50 to 500 microns; and
  c) a thickening agent,
wherein the thickening agent is added to the benefit agent in amount from 1 to 50 wt % based on the benefit agent.

The composition is suitable for cleansing and "moisturising", "conditioning" or "protection" of the skin. The benefit agent is included in the composition to moisturise, condition and/or protect the skin. By "benefit agent" is meant a substance that softens the skin (stratum corneum) and keeps it soft by retarding the decrease of its water content and/or protects the skin.

Preferred benefit agents include
  a) silicone oils, gums and modifications thereof such as linear and cyclic polydimethylsiloxanes; amino, alkyl alkylaryl and aryl silicone oils;
  b) fats and oils including natural fats and oils such as jojoba, soyabean, rice bran, avocado, almond, olive, sesame, persic, castor, coconut, mink oils; cacao fat, beef tallow, lard; hardened oils obtained by hydrogenating the aforementioned oils; and synthetic mono, di and triglycerides such as myristic acid glyceride and 2-ethylhexanoic acid glyceride;
  c) waxes such as carnauba, spermaceti, beeswax, lanolin and derivatives thereof;
  d) hydrophobic plant extracts;
  e) hydrocarbons such as liquid paraffins, petrolatum, microcrystalline wax, ceresin, squalene, squalane, and mineral oil;
  f) higher fatty acids such as lauric, myristic, palmitic, stearic, behenic, oleic, linoleic linolenic, lanolic, isostearic and poly unsaturated fatty acids (PUFA) acids;
  g) higher alcohols such as lauryl, cetyl, steryl, oleyl, behenyl, cholesterol and 2-hexadecanol alcohol;
  h) esters such as cetyl octanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, for example lauryl lactate, alkyl citrate and alkyl tartrate;
  i) essential oils such as fish oils, mentha, jasmine, camphor, white cedar, bitter orange peel, ryu, turpentine, cinnamon, bergamont, citrus unshiu, calamus, pine, lavender, bay, clove, hiba, eucalyptus, lemon, starflower, thyme, peppermint, rose, sage, menthol, cineole, eugenol, citral, citronelle, borneol, linalool, geraniol, evening primrose, camphor, thymol, spirantol, pinene, limonene and terpenoid oils;
  j) lipids such as cholesterol, ceramides, sucrose esters and pseudo-ceramides as described in European Patent Specification No. 556 957;
  k) vitamins such as vitamin A and E, and vitamin alkyl esters, including those vitamin C alkyl esters;
  l) sunscreens such as octyl methoxyl cinnamate (Parsol MCX) and butyl methoxy benzoylmethane (Parsol 1789);
  m) Phospholipids; and
  n) mixtures of any of the foregoing components.

The benefit agent may be incorporated in a carrier in the compositions of the invention, particularly if it is likely to suffer detrimental interactions with other components of the composition. Benefit agents for which such detrimental interactions may occur include lipids; alkyl lactates; sunscreens; esters such as isopropyl palmitate and isopropyl myristate; and vitamins. The carrier can, for example, be a silicone or hydrocarbon oil which is not solubilised/micellised by the surface active phase and in which the benefit agent is relatively soluble.

Particularly preferred benefit agents include silicone oils, gums and modifications thereof, esters such as isopropyl palmitate and myristate and alkyl lactates.

The benefit agent is preferably present in amount of from 0.1 to 15 wt %, most preferably from 0.2 to 10 wt %, more. preferably from 0.5 to 7 wt %.

An advantage of the composition according to the invention is that, during use, it deposits benefit agent onto the skin at a level which results in a perceivable benefit. Without being bound by theory, it is believed the benefit agent is dispersed into large pools during dilution of the composition in use and these pools deposit readily onto the skin.

In WO 94/01084 and WO 94/01085 the composition are structured by the presence of at least 5% insoluble solid fatty acid soap. However, it is believed that such high levels of solid phase material may adversely affect the amount of benefit agent deposited onto the skin. Thus, in the present invention it is preferred that the composition is substantially free of solid soap, by which is meant the level of solid soap is below 1 wt %.

Suitable thickening agents for the benefit agent include polacrylates; fumed silica natural and synthetic waxes, alkyl silicone waxes such as behenyl silicone wax; aluminium silicate; lanolin derivatives such as lanesterol; higher fatty alcohols; polyethylenecopolymers; narogel; polyammonium stearate; sucrose esters; hydrophobic clays; petrolatum; hydrotalcites; and mixtures thereof.

Hydrotalcites are materials of general formula $$[M_mN_n(OH)_{2(m+n)}]^{n+}X^{m-}{}_{n/m}\cdot yH_2O$$

where
M is a divalent metal ion e.g. $Mg^{2+}$;
N is a trivalent metal ion e.g. $Al^{3+}$;
X is an exchangeable anion e.g. $CO_3^-$, $NO_3^-$, stearate, cinnimate;
m is the number of divalent metal ions; and
n is the number of trivalent metal ions.

Particularly preferred thickening agents for the benefit agent include silica, alkyl silicone waxes, paraffin wax higher fatty alcohols, petroleum jelly and polyethylenecopolymers.

Whilst some materials can function as both a benefit agent and a thickener therefor it will be appreciated that the benefit and thickening function cannot be provided by the same component. However, it will be understood that where the composition comprises two or more benefit agents one of said benefit agents could also function as a thickening agent.

Preferably the amount of thickening agent is from 4 to 25% wt based on the level of benefit agent.

Although the compositions of the invention may be self-structuring preferably they will also comprise a structurant, i.e. a material added to increase the viscosity at zero shear. Suitable materials include swelling clays, for example laponite; fatty acids and derivatives hereof and, in particular fatty acid monoglyceride polyglycol ethers; cross-linked polyacrylates such as Carbopol (™) (polymers available from Goodrich); acrylates and copolymers thereof, polyvinylpyrrolidone and copolymers thereof; polyethylene imines; salts such as sodium chloride and ammonium sulphate; sucrose esters; gellants; and mixtures thereof.

Of the clays particularly preferred are synthetic hectorite (laponite) clay used in conjunction with an electrolyte salt capable of causing the clay to thicken. Suitable electrolytes include alkali and alkaline earth salts such as halides, ammonium salts and sulphates.

The compositions according to the invention may also comprise a thickening agent in addition to the thickening agent added to the benefit agent, i.e. a material which maintains the viscosity of the composition as the shear rate thereof is increased during use. Suitable materials include cross-linked polyacrylates such as Carbopol (™) (polymers available from Goodrich); fatty acids and derivatives thereof and, in particular, fatty acid monoglyceride polyglycol ethers; natural gums including alginates, guar, xanthan and polysaccharide derivatives including carboxy methyl cellulose and hydroxypropyl guar; propylene glycols and propylene glycol oleates; salts such as sodium chloride and ammonium sulphate; glycerol tallowates; and mixtures thereof.

Further examples of structurants and thickeners are given in the International Cosmetic Ingredient Dictionary, Fifth Edition, 1993, published by CTFA (The Cosmetic, Toiletry & Fragrance Association), incorporated herein by reference.

The surface active agent Can be selected from any known surfactant suitable for topical application to the human body. Mild surfactants, i.e. surfactants which do not damage the stratum corneum, the outer layer of skin, are particularly preferred.

One preferred anionic detergent is fatty acyl isethionate of formula:

$$RCO_2CH_2CH_2SO_3M$$

where R is an alkyl or alkenyl group of 7 to 21 carbon atoms and M is a solubilising cation such as sodium, potassium, ammonium or substituted ammonium. Preferably at least three quarters of the RCO groups have 12 to 18 carbon atoms and may be derived from coconut, palm or a coconut/palm blend.

Another preferred anionic detergent is alkyl ether sulphate of formula:

$$RO(CH_2CH_2O)_nSO_3M$$

where R is an alkyl group of 8 to 22 carbon atoms, n ranges from 0.5 to 10, especially from 1.5 to 8, and M is a solubilising cation as defined above.

Other possible anionic detergents include alkyl glyceryl ether sulphate, sulphosuccinates, taurates, sarcosinates, sulphoacetates, alkylphosphate, alkyl phosphate esters and acyl lactylate, alkyl glutamates and mixtures thereof.

Sulphosuccinates may be monoalkyl sulphosuccinates having the formula:

$$R^5O_2CCH_2CH(SO_3M)CO_2M;$$

and amido-MEA sulphosuccinates of the formula:

$$R^5CONHCH_2CH_2O_2CCH_2CH(SO_3M)CO_2M;$$

wherein $R^5$ ranges from $C_8$–$C_{20}$ alkyl, preferably $C_{12}$–$C_{15}$ alkyl and M is a solubilising cation.

Sarcosinates are generally indicated by the formula:

$$R^5CON(CH_3)CH_2CO_2M,$$

wherein $R^5$ ranges from $C_8$–$C_{20}$ alkyl, preferably $C_{12}$–$C_{15}$ alkyl and M is a solubilising cation.

Taurates are generally identified by the formula:

$$R^5CONR^6CH_2CH_2SO_3M,$$

wherein $R^5$ ranges from $C_8$–$C_{20}$ alkyl, preferably $C_{12}$–$C_{15}$ alkyl, $R^6$ ranges from $C_1$–$C_4$ alkyl, and M is a solubilising cation.

Harsh surfactants such as primary alkane sulphonate or alkyl benzene sulphonate will generally be avoided.

Suitable nonionic surface active agents include alkyl polysaccharides, lactobionamides, ethyleneglycol esters, glycerol monoethers, polyhydroxyamides (glucamide), primary and secondary alcohol ethoxylates, especially the $C_{8-20}$ aliphatic alcohols ethoxylated with an average of from 1 to 20 moles of ethylene oxide per mole of alcohol.

Mixtures of any of the foregoing surface active agents may also be used.

The surface active agent is preferably present at a level of from 1 to 35 wt %, preferably 3 to 30 wt %.

It is also preferable that the composition includes from 0.5 to 15 wt % of a cosurfactant agent with skin-mildness benefits. Suitable materials are zwitterionic detergents which have an alkyl or alkenyl group of 7 to 18 carbon atoms and comply with an overall structural formula:

$$R^1 {+\!\!\!\!\!-} \overset{O}{\underset{\|}{C}} -NH(CH_2)_m {-\!\!\!\!\!+}_{\overline{n}} \overset{R^2}{\underset{R^3}{\overset{|}{N^+}}} -X-Y$$

where $R^1$ is alkyl or alkenyl of 7 to 18 carbon atoms; $R^2$ and $R^3$ are each independently alkyl, hydroxyalkyl or carboxyalkyl of 1 to 3 carbon atoms;
m is 2 to 4;
n is 0 or 1;
X is alkylene of 1 to 3 carbon atoms optionally substituted with hydroxyl, and Y is —CO$_2^-$ or —SO$_3^-$.

Zwitterionic detergents within the above general formula include simple betaines of formula:

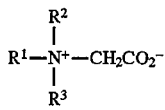

and amido betaines of formula:

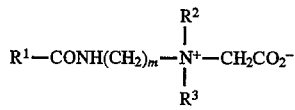

where m is 2 or 3.

In both formulae R$^1$, R$^2$ and R$^3$ are as defined previously. R$^1$ may, in particular, be a mixture of C$_{12}$ and C$_{14}$ alkyl groups derived from coconut so that at least half, preferably, at least three quarter of the groups R$^1$ has 10 to 14 carbon atoms. R$^2$ and R$^3$ are preferably methyl.

A further possibility is a sulphobetaine of formula:

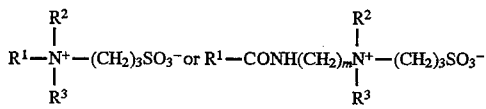

where m is 2 or 3, or variants of these in which —(CH$_2$)$_3$SO$_3^-$ is replaced by

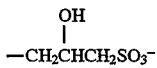

R$^1$, R$^2$ and R$^3$ in these formulae are as defined previously.

Furthermore, the benefit agent may also function as a carrier to deliver efficacy agents to skin treated with the compositions of the invention. This route is particularly useful for delivering efficacy agents which are difficult to deposit onto the skin or those which suffer detrimental interactions with other components in the composition. In such cases the carrier is a often a silicone or hydrocarbon oil which is not solubilised/micellised by the surface active phase and in which the efficacy agent is relatively soluble. Examples of such efficacy agents include anti-viral agents; hydroxycaprylic acids; pyrrolidone; carboxylic acids; 2,4, 4'-trichloro-2'-hydroxydiphenyl ether (Irgasan DP300); 3,4, 4'-trichlorocarbanilide; salicylic acid; benzoyl peroxide; perfumes; essential oils; germicides and insect repellants such as N,N-dimethyl m-toluamide (DEET); and mixtures thereof.

Compositions of the invention may be formulated as products for washing the skin, for example bath or shower gels, hand washing compositions, facial washing liquids; pre-and post-shaving products; rinse-off, wipe-off and leave-on skin-care products.

The compositions of the invention will generally be pourable liquids or semi-liquids eg pastes and will preferably have a viscosity in the range 1000 to 100,000 mPas measured at a shear rate 10 s$^{-1}$ and 25° C. in a Haake Rotoviscometer RV20.

The compositions of the invention will preferably exhibit a Newtonian viscosity at a shear stress of 0.01 Pa, at 25° C., of at least 5,000 Pas, preferably greater than 10,000 Pas.

The above-mentioned characteristic viscosity measurements may be determined exactly (as in the case of the non-zero shear viscosities) using, for example a Carrimed CSL 100 low stress rheometer or obtained from an extrapolation according to the Cross Model, (see J of the Chemical Engineer, 1993, paper entitled "Rheology for the Chemical Engineer" by H. Barnes) as in the case of zero shear rate.

Other typical components of the compositions include opacifiers, preferably 0.2 to 2.0 wt %; preservatives, preferably 0.2 to 2.0 wt % and perfumes, preferably 0.5 to 2.0 wt %.

According to a further aspect of the invention there is provided a process for preparing compositions according to the invention comprising:

a) forming a base composition comprising at least one surface active agent selected from anionic, nonionic, zwitterionic and cationic surface active agents and mixtures thereof;

b) adding a thickening agent to the benefit agent in an amount from 1 to 50% wt, based on the benefit agent; and c) mixing the base formulation of step a) with the benefit agent.

The invention will be further illustrated by reference to the following non-limiting examples.

EXAMPLES

In the examples:

Alkylpolyglucoside was Plantaren 2000 ex Henkel Behenyl alcohol was Nacol 22-97 ex Condea.

Behenyl silicone wax was Cire 71649 ex Rhone Poulenc.

Coco amidopropyl betaine was Amonyl BA 380 ex Seppic.

Cross-linked polyacrylate was Carbopol ETD 2020 ex Goodrich.

Guar hydroxypropyl trimonium chloride was Jaguar C-13-S ex Meyhall.

Hydrotalcite was hydrotalcite containing IPP Multigel IPP ex Guilini Chemie GmbH IPP (isopropyl palmitate) was ESTOL 1517 ex Unichema.

Lauryl lactate was Crodamol LL ex Croda Chemicals.

MEA suphosuccinate was witco 5690 ex Witco.

Polyethylene AC617 was from A–C Performance Additives. Silica was a hydrophobically modified silica, Aerosil R972 ex Degussa.

The silicone oils were all DC200, a polydimethylsiloxane ex Dow Corning, but with a varying viscosities as stated below.

Silicone oil emulsion was BC 92/057 ex Basildon. Sodium lauryl ether sulphate was Genapol ZRO ex Hoechst

Example I

In this example, the effect of thickening a silicone oil benefit agent with silica on the deposition of silicone oil onto the skin was examined.

The following method was used to determine the amount of benefit agent deposited onto full thickness porcine skin (5 ×15 cm) treated with compositions according to the invention.

The skin was prehydrated and then 0.5 ml of the product applied to it. The product was lathered for 10 seconds and then rinsed for 10 seconds under running water.

Thereafter the skin was wiped once with a paper towel to remove excess water.

2 minutes after drying a strip of adhesive tape was pressed onto the skin for 30 seconds by applying a constant load of 100 g.cm$^{-2}$. The adhesive tape employed was J-Lar Super-clear (™) tape having a width of 2.5 cm. In total ten strips of tape were applied to adjacent sites on the skin.

In this test procedure silicone which has deposited on the skin will subsequently be transferred to the tape along with some of the outer layer of the skin.

The amounts of silicon and skin adhering to the tape are determined by means of X-ray fluorescence spectroscopy.

The tape strips are placed in an X-ray fluorescence spectrometer with the adhesive side facing the beam of this machine. A mask is applied over the tape to define a standardised area in the middle of the tape which is exposed to the X-ray beam. The sample chamber of the machine is placed under vacuum before making measurements and the spectrometer is then used to measure the quantities of silicon and sulphur. The sulphur is representative of the amount of skin which has transferred to the tape.

The amounts of silicon and sulphur observed with a clean piece of adhesive tape are subtracted from the experimental measurements. The experimental measurements for the average levels of sulphur and silicon are expressed as a ratio of silicon to sulphur. From this ratio it is possible to determine silicone oil-deposition per unit area of skin.

A base shower gel formulation having the following composition was prepared.

|  | % wt |
| --- | --- |
| Sodium lauryl ether sulphate | 4.00 |
| Sodium coco amido propyl betaine | 1.00 |
| Alkylpolyglucoside | 5.00 |
| Sorbic acid | 0.37 |
| Trisodium citrate dihydrate | 0.49 |
| Cross-linked polyacrylate | 0.9 |
| Thickener* | ~1 |
| 5N NaOH** | ~1 |
| Water + minors | to 100 |

*Thickener added to give the required viscosity (~5000 mPas at 10 s$^{-1}$ and 25° C.)
**NaOH was added to adjust the pH of the composition to pH 5.3.

The composition was prepared by dispersing the polyacrylate in excess water. Thereafter sorbic acid and trisodium citrate dihydrate were added to the resulting polymer dispersion. The three surface active agents were mixed and the resulting mix added to the polymer dispersion. Thereafter minors were added. The viscosity of the resulting composition was measured at a shear rate of 10 s$^{-1}$ at 25° C. and thickener added until the required viscosity obtained.

Two Harvard 44 syringe pumps were used to infuse the base formulation and the benefit agent, silicone oil. Silicone oil was present at a level of 5 wt % based on the total composition. One syringe was filled with the base formulation and the other with silicone oil. The syringes were then inserted into the syringe pump and the infusion rate set at 5:95 oil:base. The oil and base were forced through a static in-line mixer and a composition with oil particles of the required size obtained. The size of the particles can be controlled by the diameter of the static mixer, the flow rate and length of the mixer tube. The size of the particles can be determined using a Malvern Mastersizer.

Silicone deposition from the compositions according to the invention was measured by the test procedure described above and compared with that from a similar composition (A) comprising a silicone oil emulsion having a viscosity of 60000 mPas at 10 s$^{-1}$ and 25° C.

Comparative Composition (Composition A)

|  | % wt |
| --- | --- |
| Sodium lauryl ether sulphate | 13.00 |
| Coco amidopropyl betaine (CAPB) | 2.00 |
| Silicone oil emulsion | 5.00 |
| Guar hydroxypropyl trimonium chloride | 0.10 |
| Sorbic acid | 0.37 |
| Sodium citrate dehydrate | 0.49 |
| Sodium chloride* | ~2 |
| Citric acid** | ~0.01 |
| Water + minors | to 100 |

*level can be varied in order to give the required viscosity of 5000 mPas at 10 s$^{-1}$ and 25° C.
**level can be varied in order to give the required pH.

The following results were obtained.

|  | % Silica added | Si:S ratio | particle size/μm |
| --- | --- | --- | --- |
| Comparison | 0 | 0.9 | 0.5 |
| Ia | 8.3 | 63.9 | 424 |
| Ib | 9.7 | 22.2 | 354 |
| Ic | 4.7 | 21.3 | 341 |
| Id | 6.1 | 11.5 | 289 |

The results demonstrate the advantage, in terms of deposition of silicone, using a composition comprising a thickened silicone oil over a composition comprising a unthickened silicone oil.

Example II

Example I was repeated except that the benefit agent used was IPP (isopropylpalmitate). The IPP was thickened with three different thickeners at a level of 10% by weight based on the IPP.

The following method was used to determine the amount of IPP deposited onto full thickness porcine skin (5×15 cm pieces) treated with compositions according to the invention. The skin was treated and washed with the compositions according to the invention by the same method as described for example I. Thereafter the skin was extracted with ethanol three times (3 ml per extract) and the extract made up to 10 g and submitted for Gas Chromatography analysis to determine the amount of IPP deposited.

The following results were obtained:

| thickener | deposition/ppm |
| --- | --- |
| none | 6.1 |
| polyethylene AC617 | 441.9 |
| behenyl silicone wax | 138.1 |
| hydrotalcite | 59.1 |

The results demonstrate the increased deposition of IPP obtained when the IPP is thickened.

Example III

In this example the benefit agent used was lauryl lactate.

The following method was used to determine the amount of lauryl lactate deposited onto skin treated with compositions according to the invention containing lauryl lactate.

Porcine full thickness skin was prehydrated and then 0.20 g of the product and 0.8 g of water applied to it. The skin was washed for 30 seconds and then rinsed for 10 seconds under running water.

Thereafter the skin was wiped once with a paper towel to remove excess water. 30 seconds after drying 5 strips of Desquame tape were applied to the skin sequentially for 10 seconds.

The strips were then removed from the skin and hydrolysed in 2 ml of NaOH (0.5M) at 60° C. for 60 minutes. They were then neutralised with 2 ml HCl (0.5M) and in Sorensens phosphate buffer (pH 7.0). The total lauryl lactate and the protein content of the tapes, representative of the lauryl lactate transferred to the skin, was determined using Sigma diagnostic assay Kits 735/10 and 690. A solution containing the assay and treated strips was prepared and the absorbance at 540 nm measured in a UV spectrometer.

The base formulation for the following experiments was:

|  | Wt % |
|---|---|
| MEA sulphosuccinate | 11.7 |
| Cross-linked polyacrylate | 0.3 |
| Sodium cocoyl isethionate | 8.5 |
| Coco amidopropyl betaine | 15.8 |
| Water and minors | to 100 |

It was prepared by dispersing the polyacrylate in excess water. A premix of the three surfactants was then added to the polymer dispersion. Thereafter minors were added.

The following benefit agent/thickener combination was used:

|  |  | wt % | Droplet size/μm |
|---|---|---|---|
| X | Lautyl lactate | 85 | 172.2 |
|  | Polyethylene AC617 | 15 |  |

The mixture X was prepared by heating the two components together to a temperature of ~110° C. to melt in the polyethylene. The mixture was then allowed to cool before being used.

An emulsion of the base formulation and thickened benefit agent, was applied to the skin using the test procedure described above.

The following results were obtained:

|  | lactate/Absorbance units ($\times 10^{-3}$) |
|---|---|
| Untreated skin | 81 |
| base formulation (no lauryl lactate) | 63 |
| base + 5%*X | 128 |
| base + 5% lauryl lactate | 102 |
| base + 10%*X | 154 |
| base + 10% lauryl lactate | 107 |

*based on the total composition

In a separate set of experiments, but with the same base formulation as described above, the effect of a range of thickening agents (all at a level of 5% wt based on the lauryl lactate) on the deposition of lauryl lactate was examined. The lauryl lactate or thickened lauryl lactate was added to the base formulation at a level of 5wt %.

|  | lactate/Absorbance units ($\times 10^{-3}$) |
|---|---|
| lauryl lactate (no thickener) | 112 |
| lauryl lactate + paraffin wax | 148 |
| lauryl lactate + behenyl alcohol | 152 |
| lauryl lactate + petroleum jelly | 148 |
| lauryl lactate + polyethylene AC617 | 129 |
| lauryl lactate + behenyl silicone wax | 167 |

The results demonstrate the benefit of thickening the benefit agent with a thickening agent.

We claim:

1. An aqueous liquid cleansing and moisturizing composition comprising:

(a) a surface active agent selected from the group consisting of anionic, nonionic, zwitterionic and cationic surface active agents, and mixtures thereof;

(b) a benefit agent having a weight average particle size in the range 50 to 500 microns;

(c) a thickening agent; and (d) less than one percent by weight solid soap;

wherein the thickening agent is added to the benefit agent in amount from 1 to 50% wt., based on the benefit agent.

2. A composition according to claim 1 wherein the thickening agent is selected from the group consisting of polyacrylates; silica, natural and synthetic waxes, alkyl silicone waxes; aluminium silicate; lanolin derivatives; higher fatty alcohols; polyethylenecopolymers; narogel; polyammonium stearate; sucrose esters; hydrophobic clays; petrolatum; hydrotalcites; and mixtures thereof.

3. A composition according to claim 1 wherein the composition is structured with a structurant selected from the group consisting of swelling clays; cross-linked polyacrylates; acrylates and copolymers thereof; polyvinylpyrrolidone and copolymers thereof; polyethylene imines; salts; sucrose esters; and gellants.

4. A composition according to claim 1 wherein the benefit agent is selected from the group consisting of silicone oils; gums; fats; oils waxes; hydrophobic plant extracts; hydrocarbons; fatty acids; alcohols; esters; essential oils; lipids; phospholipids; vitamins; sunscreens; and mixtures thereof.

5. A composition according to claim 1 comprising 0.1 to 15 wt % of the benefit agent.

6. A composition according to claim 1 wherein the benefit agent functions as a carrier to deliver efficacy agents to skin treated with the composition.

7. A composition according to claim 1 comprising 1 to 35 wt % of the surface active agent.

8. A composition according to claim 1 further comprising a cosurfactant selected from the group consisting of betaines, amidobetaines and sulphobetaines.

9. A process for preparing a composition according to claim 1, comprises:

(a) forming a base composition comprising at least one surface active agent selected from the group consisting of anionic, nonionic, zwitterionic and cationic surface active agents and mixtures thereof and less than one percent by weight solid soap;

(b) adding a thickening agent to the benefit agent in an amount from 1 to 50 wt. %, based on the benefit agent; and (c) mixing the base formulation of step (a) with the benefit agent.

10. A method of depositing a benefit agent from an aqueous liquid cleansing and moisturizing composition, the method comprising providing the said benefit agent in a composition comprising:

(a) a surface active agent selected from anionic, nonionic, zwitterionic and cationic surface active agents, and mixtures thereof;

(b) a benefit agent having a weight average particle size in the range 50 to 500 microns;

(c) a thickening agent, wherein the thickening agent is added to the benefit agent in amount from 1 to 50% wt., based on the benefit agent; and (d) less than one percent by weight solid soap.

* * * * *